United States Patent [19]

DiPippo

[11] 4,259,499

[45] Mar. 31, 1981

[54] METHOD FOR PREPARING 2-SULFOCHLORIDE BENZOATES AND THE USE OF SAME IN THE PREPARATION OF SACCHARIN

[75] Inventor: Carmine A. DiPippo, Longmeadow, Mass.

[73] Assignee: James River Graphics Inc., South Hadley, Mass.

[21] Appl. No.: 899,498

[22] Filed: Apr. 24, 1978

Related U.S. Application Data

[60] Continuation of Ser. No. 760,382, Jan. 18, 1977, abandoned, which is a division of Ser. No. 620,281, Oct. 7, 1975, Pat. No. 4,042,600, which is a continuation of Ser. No. 298,226, Oct. 17, 1972, abandoned.

[51] Int. Cl.³ .......................... C07D 275/06
[52] U.S. Cl. ........................ 548/211; 260/141; 560/14; 560/18
[58] Field of Search .......................... 548/211

[56] References Cited

U.S. PATENT DOCUMENTS 2,667,503   1/1954   Senn ..................... 548/211 X

FOREIGN PATENT DOCUMENTS 910889   5/1954   Fed. Rep. of Germany ........... 548/211

OTHER PUBLICATIONS

Meerwein et al., Chemische Berichte, vol. 90, No. 6, pp. 841-852, (1957).

Primary Examiner—Donald G. Daus
Assistant Examiner—Diana G. Rivers
Attorney, Agent, or Firm—Burns, Doane, Swecker & Mathis

[57] ABSTRACT

A method of preparing 2-sulfochloride benzoates which comprises diazotizing any anthranilate to form a 2-diazonium chloride benzoate and thereafter reacting said 2-diazonium chloride benzoate with sulfur dioxide to form a 2-sulfochloride benzoate. The invention also provides for the total synthesis of saccharin which comprises pyrolyzing a 2-sulfochloride benzoate to form an o-sulfobenzoic anhydride and then ammonolyzing the o-sulfobenzoic anhydride to saccharin which is free of bitter tasting contaminants from such reactants.

7 Claims, No Drawings

METHOD FOR PREPARING 2-SULFOCHLORIDE BENZOATES AND THE USE OF SAME IN THE PREPARATION OF SACCHARIN

CROSS REFERENCE TO RELATED APPLICATIONS

This application is a continuation of application U.S. Ser. No. 760,382, filed on Jan. 18, 1977, now abandoned which is, in turn, a division of application U.S. Ser. No. 620,281, filed on Oct. 7, 1975 and issued as U.S. Pat. No. 4,042,600 on Aug. 16, 1977, said application being a continuation of U.S. Ser. No. 298,226, filed Oct. 17, 1972 and since abandoned.

BACKGROUND OF THE INVENTION

The present invention relates to a method of preparing 2-sulfochloride benzoates, and, more especially, relates to a method of preparing such compounds which comprises diazotizing an anthranilic acid ester to form a 2-diazonium chloride benzoate and then reacting the 2-diazonium chloride benzoate with sulfur dioxide to form the 2-sulfochloride benzoate. This invention also relates to a method of synthesizing saccharin which comprises pyrolyzing a 2-sulfochloride benzoate at elevated temperatures and then ammonolyzing the resulting o-sulfobenzoic anhydride to saccharin.

Saccharin is variously known as o-benzosulfimide; gluside; benzoylsulfonic imide; and is the anhydride of o-sulfimide benzoic acid having the formula:

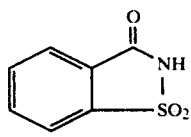

Saccharin is employed in the manufacture of syrups, medicine (substitute for sugar), soft drinks, foods, and the like, and is a nonnutritive sweetener which can readily be converted to sodium or soluble saccharin, and is a white, crystalline powder. It has an exceedingly sweet taste (500 times that of cane sugar), a melting point of about 226° C. to 230° C., and is soluble in amyl acetate, ethyl acetate, benzene and alcohol; slightly soluble in water, chloroform and ether.

Saccharin has been made from toluene by the following series of reactions:

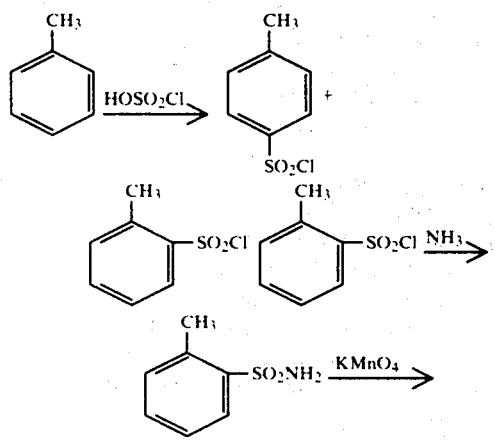

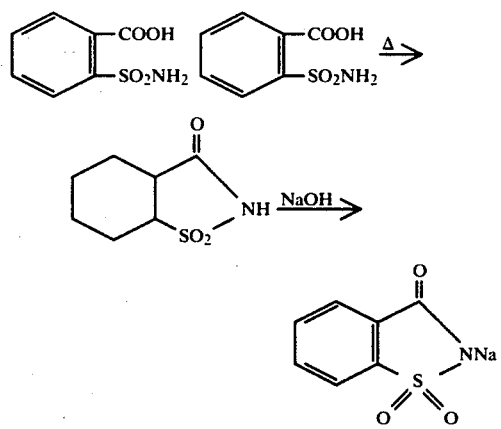

The imide is converted to the sodium salt to increase the solubility in water. Saccharin can also be prepared by converting a mixture of toluene sulfonic acids into the sodium salt, then by distillation with phosphorus trichloride and chlorine to obtain the ortho-toluene sulfonyl chloride, which by means of ammonia is converted into ortho-toluenesulfamide. This is oxidized with permanganate, treated with acid and saccharin crystallized out. It is reported that the slight bitter taste associated with the saccharin prepared by either of the above methods is caused by the presence of o-toluamide. Moreover, the disposal of the p-toluenesulfonyl chloride obtain by-product in the above processes has also been a problem.

Both of these objections have been attempted to be overcome by two more recent processes, the first [A] commencing with thianaphthene (prepared from styrene and sulfur) and the other [B] with anthranilic acid, as follows [see Noller, *Chemistry of Organic Compounds,* 2nd Edition, pp. 556–7 (1957)]:

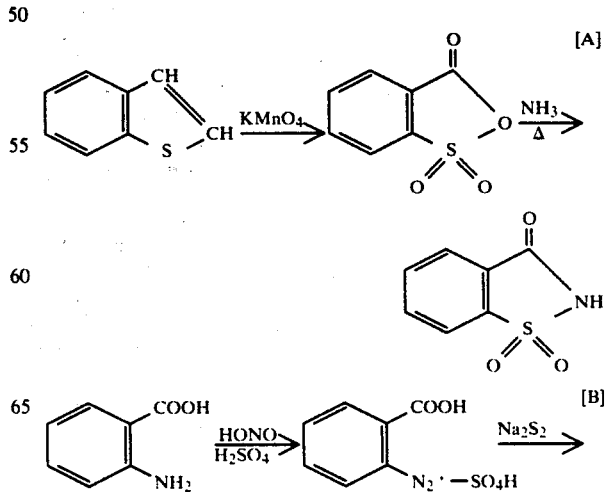

-continued

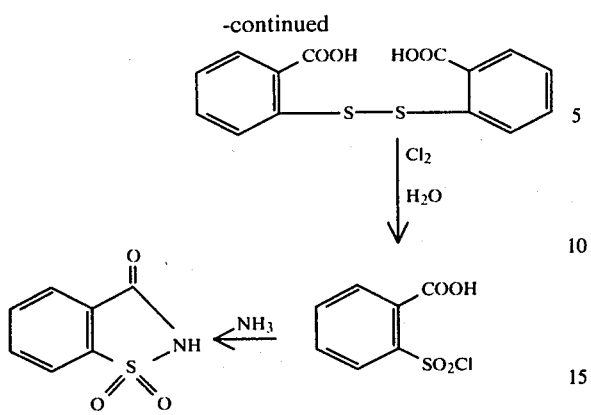

Nevertheless, it too is reported that even when utilizing these alternate routes there still is a slight bitter taste associated with the saccharin, here probably caused by the presence of certain trace contaminants.

SUMMARY OF THE INVENTION

Accordingly, it is an immediate object of this invention to provide an improved method for the total synthesis of saccharin.

Another object of this invention is to provide for the total synthesis of saccharin, which recovered saccharin product is free of those bitter tasting contaminants heretofore characterizing the usual saccharin forms.

Still another object of this invention is to provide an improved process for the preparation of the 2-sulfochloride benzoate intermediates from readily available and inexpensive reactants.

In attaining the objects of this invention, one feature resides in the pyrolysis of various 2-sulfochloride benzoates to yield o-sulfobenzoic anhydride according to the reaction scheme:

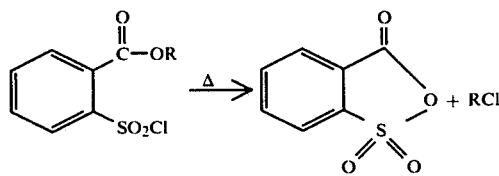

The immediately above reaction may be carried out in the vapor phase by passing the reactant ester through a hot tube and condensing out the product in a continuous fashion. It may also be carried out by heating the reactant ester under reduced pressure and distilling off the product, or by heating the reactant ester alone, or by heating the reactant ester in a suitable high boiling or other solvent, or by pyrolyzing the reactant ester in a sealed tube to aid in trapping the volatile organochloride by-product.

The reactant 2-sulfochloride benzoates can be made easily from starting materials which are readily available. For instance, they may be made by reacting esters of dithiodibenzoic acid with chloride water. They may also be made by reacting 2-diazonium chloride benzoates with sulfur dioxide in the presence of cuprous chloride and acetic acid. 2-Diazonium chloride benzoates can be made by diazotizing esters of anthranilic acid.

Other objects, features, and advantages of this invention will become more apparent from the description which follows.

DETAILED DESCRIPTION OF THE INVENTION

In one embodiment in accordance with this invention, the 2-sulfochloride benzoate precursors are prepared by diazotizing the corresponding anthranilates, advantageously the lower alkyl, e.g., methyl, ethyl or isobutyl, or aralkyl, e.g., benzyl, anthranilates. The diazotizing reaction is conventional and can be effected in standard, known fashion, for example, by treatment, in concentrated hydrochloric acid, with nitric oxides or compounds which release such oxides, e.g., nitrites such as sodium nitrite, or nitrous acid. The resultant 2-diazonium chloride benzoates, useful dye intermediates, are converted into the corresponding 2-sulfochloride benzoate by reaction with sulfur dioxide in the presence of cuprous chloride and acetic acid. Compare Meerwein et al., *Berichte*, 90, 841 (1957).

The foregoing "diazo route" to the 2-sulfochloride benzoates, and wherein the anthranilate starting materials are readily synthesized in known manner from an alcohol and isatoic anhydride, may be represented by the following series of reactions:

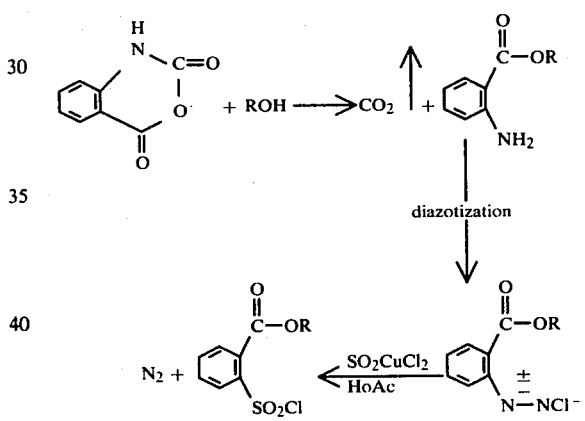

wherein R can be any one of a variety of organic radicals, typically hydrocarbon radicals, inert to the respective reactions, such as lower alkyl and lower cycloalkyl having from 1 to 8 carbon atoms, e.g., methyl, ethyl, n-propyl, i-propyl, n-butyl, i-butyl, sec-butyl, t-butyl, cyclohexyl; aryl having from 6 to 10 carbon atoms, e.g., phenyl; aralkyl wherein the "aryl" and "alkyl" components are as previously defined, e.g., benzyl; and alkenyl having from 2 to 8 carbon atoms, e.g., allyl.

Albeit somewhat less facile than the "diazo route", the 2-sulfochloride benzoate precursors can also be prepared by reacting the corresponding esters of dithiodibenzoic acid, advantageously dibenzyl dithiodibenzoate, with chloride water.

The foregoing "dithio route" to the 2-sulfochloride benzoates, and wherein the dithiodibenzoate starting materials (useful in and of themselves as antioxidants and rubber accelerators) are also readily synthesized in known manner from an alcohol and dithiodibenzoyl dichloride, may be represented by the following series of reactions:

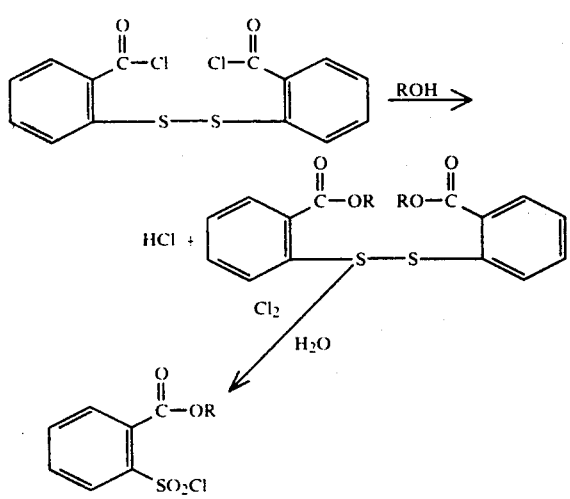

wherein R is as heretofore defined.

Pyrolysis of the subject 2-sulfochloride benzoates, whether prepared via the aforesaid "diazo route" or "dithio route", or any other route whatsoever, advantageously takes place at a temperature in the range of from about 150° C. to about 400° C., albeit there exist certain preferred values within this range for the pyrolysis of a given ultimate species, e.g., about 165° C. for pyrolysis of either isopropyl or benzyl 2-sulfochloride benzoate, and about 225° C. for pyrolysis of isobutyl 2-sulfochloride benzoate. And, as heretofore mentioned, the following pyrolysis reaction:

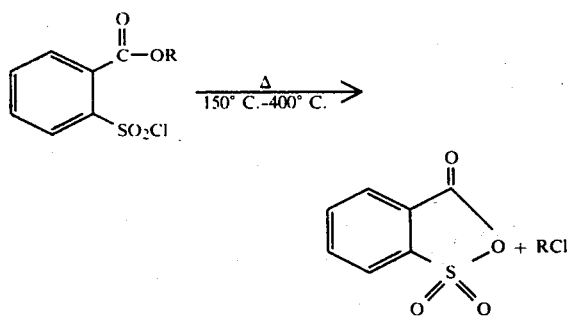

wherein R is as previously defined, exhibits the advantages over the known prior art in that this reaction may easily be carried out continuously, the same does not involve the formation of such by-products as ammonium chloride which makes isolation of the desired anhydride difficult, the pyrolysis does not require the use of undesirable reagents such as thionyl chloride or toxic solvents such as benzene or chlorobenzene, and the product o-sulfobenzoic anhydride can be directly obtained in high yields and in a relatively pure state.

The o-sulfobenzoic anhydride produced by pyrolysis of the 2-sulfochloride benzoates is readily converted into essentially pure saccharin free of bitter tasting contaminants by simple ammonolysis, for example, by ammonolysis with a concentrated solution of ammonium hydroxide, namely:

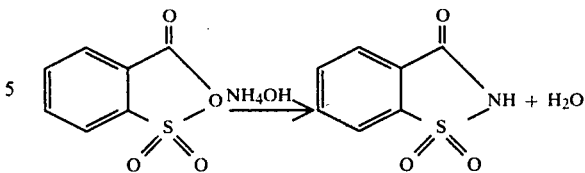

In order to further illustrate the present invention and the advantages thereof, the following specific examples are given, it being understood that the same are intended merely as illustrative and in no wise limitative.

EXAMPLE 1

Pyrolysis of Isobutyl-2-Sulfochloride Benzoate Prepared Via "Diazo Route"

A slurry of 96.6 g. of isobutyl anthranilate (prepared by reaction of isobutyl alcohol with isatoic anhydride) in 170 ml. of concentrated HCl was diazotized at a temperature of less than 10° C. with a 40° aqueous solution of sodium nitrite until an end-point was reached with Green Reagent.

This reaction mixture was then filtered through a fritted glass filter and the cold filtrate poured into a cold mixture consisting of 191 g. of sulfur dioxide and 6.6 g. of cuprous chloride in 400 ml. of glacial acetic acid. This reaction mixture was removed from the ice bath and allowed to warm us to 35° C., much evolution of gas was observed.

The above reaction mixture was then poured into 2 liters of water, causing the separation of a light brown liquid. This mixture was extracted with 500 ml. of methylene chloride. The organic phase was separated, washed three times with 250 ml. portions of 5% sodium bicarbonate, and dried with anhydrous magnesium sulfate. After filtering off the drying agent and removing the solvent under vacuum with a rotary evaporator, Rota-Vap, 76 g. of crude product remained, namely isobutyl-2-sulfochloride benzoate.

Attempted vacuum distillation of the crude product produced three fractions as the pot temperature gradually rose and distillation proceeded:

Fraction I-b.p.=79° C./1.4 mm. Gas chromatographic analysis showed this liquid to be mostly homogeneous isobutyl-2-sulfochloride benzoate.

Fraction II-b.p.=96.5° C./2 mm. Pot temp.=213° C. A small amount of white solid (o-sulfobenzoic anhydride) formed in the liquid distillate. G.C. analysis showed this fraction to consist of a mixture of o-sulfobenzoic anhydride and isobutyl-2-sulfochloride benzoate.

Fraction III-b.p.=125° C./3 mm. Pot temp.=220° C. The distillate was solid o-sulfobenzoic anhydride which solidified in the condenser and was positively identified by comparative infrared analysis.

EXAMPLE 2

Pyrolysis of Benzyl-2-Sulfochloride Benzoate Prepared Via "Dithio Route"

In a 3-necked 1-liter flask equipped with overhead stirrer, thermometer, gas inlet tube and ice-water bath, there was placed 200 ml. of water and a solution of 24.3 g. (0.05 moles) of dibenzyl dithiodibenzoate dissolved in 200 ml. of chloroform. (The dibenzyl dithiodibenzoate was prepared by reaction of dithiodibenzoyl dichloride with benzyl alcohol.) Chlorine gas was bubbled into this mixture with vigorous stirring and at an arbitrary rate. The temperature rose from 5° C. to 12° C.; after 20-25 min., the temperature dropped back to 5° C. and the reaction was stopped.

The reaction mixture was transferred to a separatory funnel and the upper water layer discarded. The organic layer was dried with anhydrous magnesium sulfate. After filtering off the drying agent and removing the solvent on a Rota-Vap, the resultant crude benzyl-2-sulfochloride benzoate was vacuum distilled. Pure o-sulfobenzoic anhydride distilled off: b.p.=100° C./0.3 mm; Pot temp.=188° C. Benzyl chloride was detected in the dry ice vapor trap by gas chromatographic analysis.

EXAMPLE 3

Ammonolysis of O-Sulfobenzoic Anhydride

The resultant o-sulfobenzoic anhydride prepared according to either of the preceding examples was cooled to 50° C. until the anhydride solidified. A concentrated solution (28%) of ammonium hydroxide was slowly added thereto and the mixture stirred at 50° C. for 2 to 3 hours; thereafter, the reaction mixture was cooled and filtered, and the saccharin was recovered therefrom in essentially pure state, free of bitter tasting contaminants.

Thus, it will be appreciated that the instant invention provides not only an improved method for the synthesis of o-sulfobenzoic anhydride by pyrolysis of the 2-sulfochloride benzoates without the formation of undesirable by-products, advantageously conducted continuously but also an improved method wherein the by-product organochlorides themselves are of significant commercial worth. For example, in the pyrolysis of methyl-2-sulfochloride benzoate, the by-product methyl chloride itself is a valuable refrigerant composition; and in the pyrolysis of benzyl-2-sulfochloride benzoate, the by-product benzyl chloride is a useful pharmaceutical intermediate. Similarly, the "R" function in the ester moiety of the 2-sulfochloride benzoates can be tailored specifically with a view towards concomitant preparation, together with the desired anhydride, of a certain RCl.

The above examples and disclosures are set forth merely for illustrating the mode and manner of the invention. And, while various modifications and embodiments can be made by those skilled in the art, in the light of this invention, such as introducing various substituents on the benzene basic nucleus of the subject benzoic compounds, or employing a bromide or other halide reactant in the pyrolysis rather than the corresponding chloride, they are made without departing from the spirit of the invention.

What is claimed is:

1. A method for the synthesis of saccharin which comprises:
   (a) pyrolyzing a 2-sulfochloride benzoate having the formula

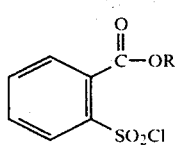

wherein R is selected from the group consisting of lower alkyl having 1 to 8 carbon atoms, lower cycloalkyl having 1 to 8 carbon atoms, aryl having from 6 to 10 carbon atoms, aralkyl, with the alkyl and aryl components thereof as previously defined, and alkenyl having from 2 to 8 carbon atoms at a temperature in the range of from about 150° C. to about 400° C. to form o-sulfobenzoic anhydride; and
   (b) subjecting said o-sulfobenzoic anhydride to ammonolysis whereby essentially pure saccharin is formed.

2. The method of claim 1 wherein the 2-sulfochloride benzoate is selected from the group consisting of isopropyl 2-sulfochloride benzoate and benzyl 2-sulfochloride benzoate.

3. The method of claim 2 wherein the pyrolysis is conducted at a temperature of about 165° C.

4. The method of claim 1 wherein the 2-sulfochloride benzoate is isobutyl 2-sulfochloride benzoate.

5. The method of claim 4 wherein the pyrolysis is conducted at a temperature of about 225° C.

6. A method for the total synthesis of saccharin which comprises:
   (a) reacting 2-diazonium chloride benzoate having the formula

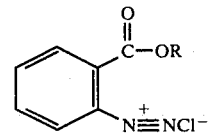

wherein R is selected from the group consisting of lower alkyl having 1 to 8 carbon atoms, lower cycloalkyl having 1 to 8 carbon atoms, aryl having from 6 to 10 carbon atoms, aralkyl, with the alkyl and aryl components thereof as previously defined, and alkenyl having from 2 to 8 carbon atoms under such conditions as to form 2-sulfochloride benzoate having the formula

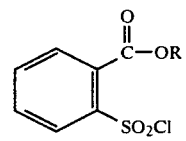

wherein R is as previously defined;
   (b) pyrolyzing said 2-sulfochloride benzoate at a temperature in the range of from about 150° C. to about 400° C. to form o-sulfobenzoic anhydride; and
   (c) subjecting said o-sulfobenzoic anhydride to ammonolysis whereby essentially pure saccharin is formed.

7. A method for the total synthesis of saccharin which comprises:
   (a) reacting a dithiobenzoate having the formula

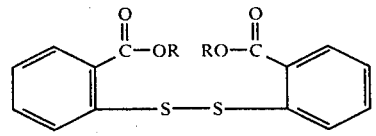

wherein R is selected from the group consisting of lower alkyl having 1 to 8 carbon atoms, lower cycloalkyl having 1 to 8 carbon atoms, aryl having from 6 to 10 carbon atoms, aralkyl, with the alkyl and aryl components thereof as previously defined, and alkenyl having from 2 to 8 carbon atoms with chlorine and water to form 2-sulfochloride benzoate having the formula

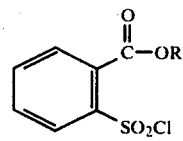

wherein R is as previously defined;

(b) pyrolyzing said 2-sulfochloride benzoate at a temperature in the range of from about 150° C. to about 400° C. to form o-sulfobenzoic anhydride; and (c) subjecting said o-sulfochloride anhydride to ammonolysis whereby essentially pure saccharin is formed.